(12) United States Patent
Watanabe et al.

(10) Patent No.: US 9,709,517 B2
(45) Date of Patent: Jul. 18, 2017

(54) GAS DETECTOR

(71) Applicant: NGK Spark Plug Co., LTD., Nagoya (JP)

(72) Inventors: Masaya Watanabe, Komaki (JP); Shoji Kitanoya, Kasugai (JP); Daisuke Ichikawa, Kani (JP); Masahiro Yamashita, Komaki (JP); Yusuke Matsukura, Nagoya (JP); Kaoru Hisada, Obu (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 177 days.

(21) Appl. No.: 14/608,605

(22) Filed: Jan. 29, 2015

(65) Prior Publication Data

US 2015/0226688 A1   Aug. 13, 2015

(30) Foreign Application Priority Data

Feb. 7, 2014   (JP) .................................. 2014-022241

(51) Int. Cl.
  *G01N 27/18*   (2006.01)
  *G01N 33/00*   (2006.01)
  (Continued)

(52) U.S. Cl.
  CPC ............. *G01N 27/18* (2013.01); *G01N 27/24* (2013.01); *G01N 27/403* (2013.01);
  (Continued)

(58) Field of Classification Search
  CPC .... G01N 27/407; G01N 27/18; G01N 27/403; G01N 27/406; G01N 27/24; G01N 27/70;
  (Continued)

(56) References Cited

U.S. PATENT DOCUMENTS

| 5,601,693 A * | 2/1997 | Davies | G01N 27/16 204/400 |
| 2005/0042141 A1* | 2/2005 | Otani | G01N 27/16 422/98 |

(Continued)

FOREIGN PATENT DOCUMENTS

JP   3387274 B   3/2003

OTHER PUBLICATIONS

Hossein Kasmai, Protection Against Electro Static Discharge in Pagers, Technical Developments Jun. 1993, Motorola Inc., vol. 19, p. 38-39.*

*Primary Examiner* — Peter Macchiarolo
*Assistant Examiner* — Timothy Graves
(74) *Attorney, Agent, or Firm* — Leason Ellis LLP

(57) ABSTRACT

A gas detector includes a detecting element, a circuit board, a housing case having a gas introduction hole, and a metal member which covers the gas introduction hole. The detecting element is disposed under the metal member. The gas detector further includes a detecting element wiring fusing prevention member which is electrically conductive and is electrically connected to a grounding line of the circuit board. The detecting element wiring fusing prevention member is disposed at a position such that the shortest distance between the metal member and the detecting element wiring fusing prevention member is smaller than that between the metal member and the detecting element.

12 Claims, 7 Drawing Sheets

(51) Int. Cl.
   *G01N 27/403* (2006.01)
   *G01N 27/24* (2006.01)
   *G01N 27/406* (2006.01)

(52) U.S. Cl.
   CPC ....... *G01N 27/406* (2013.01); *G01N 33/0009* (2013.01); *G01N 33/0016* (2013.01); *G01N 33/0027* (2013.01)

(58) Field of Classification Search
   CPC .... G01N 25/50; G01N 25/36; G01N 33/0009; G01N 33/0016; G01N 33/0027; G01N 33/005; H01L 2224/752; H01L 23/60; H01L 23/62; H01L 27/0248; H01L 2924/161; H03K 19/003; H01R 12/775; H01R 13/658; H01R 13/6471; H05K 1/0259; H02H 9/046; G06F 1/1656; H05F 3/00; H05F 3/02; A61N 1/14
   USPC ...................................................... 73/31.05
   See application file for complete search history.

(56) References Cited

U.S. PATENT DOCUMENTS

| | | | |
|---|---|---|---|
| 2006/0000258 A1* | 1/2006 | Kim | G01N 33/0009 73/23.32 |
| 2008/0185692 A1* | 8/2008 | Salzman | H01L 23/552 257/659 |
| 2012/0119346 A1* | 5/2012 | Im | H01L 21/563 257/690 |
| 2013/0209315 A1* | 8/2013 | Kimura | G01N 25/4873 422/88 |

* cited by examiner 3F-3F SECTIONAL VIEW 4F-4F SECTIONAL VIEW 6F-6F SECTIONAL VIEW

GAS DETECTOR

This application claims priority from Japanese Patent Application No. 2014-022241 filed with the Japan Patent Office on Feb. 7, 2014, the entire content of which is hereby incorporated by reference

FIELD OF THE INVENTION

The present invention relates to a technique for detecting gas to be detected.

BACKGROUND OF THE INVENTION

A conventionally known gas detector includes a rectangular tubular fixation member, a detecting element disposed within the fixation member and adapted to detect gas to be detected, and a shield cover disposed on the fixation member and having gas passage holes (refer to, for example, Japanese Patent No. 3387274).

Problem to be Solved by the Invention

The detecting element includes a heat-generating resistor (gas-detecting portion) whose resistance varies with temperature thereof. The detecting element is energized and controlled such that the heat-generating resistor assumes a resistance corresponding to a predetermined target temperature. Heat which the heat-generating resistor generates through energization thereof is conducted to gas to be detected, and the thermal conductivity of the gas to be detected varies with the concentration of flammable gas contained in the gas to be detected. When the thermal conductivity of the gas to be detected varies, a terminal-to-terminal voltage of the heat-generating resistor whose temperature is controlled at a fixed value varies accordingly. Thus, on the basis of a change in the terminal-to-terminal voltage, the concentration of the gas to be detected can be detected.

Desirably, even when static electricity is discharged to the gas detector, the gas detector is free from the occurrence of malfunction and accurately detects gas concentration. However, in the case where the gas detector is configured such that the detecting element is disposed under a gas introduction hole(s), the gas detector has potentially involved the following problem: static electricity discharged in the vicinity the gas introduction hole(s) reaches the detecting element and causes breakage of internal wiring (e.g., a resistor) of the detecting element, resulting in the occurrence of malfunction in the gas detector.

SUMMARY OF THE INVENTION

Means for Solving the Problem

The present invention has been conceived to solve the above problem and can be embodied in the following modes or application examples.
(1) According to a mode of the present invention, there is provided a gas detector comprising a detecting element for detecting flammable gas to be detected; a circuit board electrically connected to the detecting element; a housing case having a gas introduction hole for introducing the gas to be detected, and housing the detecting element and the circuit board; and a metal member disposed in the gas introduction hole and having a plurality of gas flow passages for allowing passage of the gas to be detected. The detecting element is disposed under the metal member. The gas detector is characterized by further comprising a detecting element wiring fusing prevention member which is electrically conductive and is electrically connected to a grounding line of the circuit board, and in that the detecting element wiring fusing prevention member is disposed at a position such that the shortest distance between the metal member and the detecting element wiring fusing prevention member is smaller than that between the metal member and the detecting element.

According to this gas detector, since static electricity is discharged through the detecting element wiring fusing prevention member and the grounding line of the circuit board, there can be reduced the possibility of breakage of internal wiring of the detecting element, which could otherwise be caused by static electricity.
(2) The above-mentioned gas detector may be configured as follows: the detecting element wiring fusing prevention member has a gas passage for allowing passage of the gas to be detected and is disposed in such a manner as to cover the detecting element.

According to this gas detector, since the detecting element wiring fusing prevention member covers the detecting element, the detecting element wiring fusing prevention member can not only protect the detecting element from static electricity but also physically protect the detecting element.
(3) The above-mentioned gas detector may be configured as follows: the detecting element is disposed on a base fixed on the circuit board, and the detecting element wiring fusing prevention member is fixed to the base.

According to this gas detector, the detecting element and the detecting element wiring fusing prevention member are provided on the base, whereby the detecting element wiring fusing prevention member can be positioned more easily than in the case where the detecting element wiring fusing prevention member is provided directly on the circuit board.
(4) The above-mentioned gas detector may be configured as follows: the base is electrically insulative and has a grounding electrode pad formed thereon and electrically connected to the grounding line of the circuit board, and the detecting element wiring fusing prevention member is electrically connected to the grounding electrode pad.

According to this gas detector, the detecting element wiring fusing prevention member can be grounded with use of a minimum space and without need to use an additional component(s).
(5) The above-mentioned gas detector may be configured as follows: the metal member assumes the form of a plate and is externally exposed, and the detecting element is disposed under a main surface of the metal member in the form of a plate.

The present invention is greatly effective for a gas detector configured to have a particularly high risk that static electricity discharged in the vicinity of the gas introduction hole reaches the detecting element.

The present invention can be implemented in various forms; for example, a gas detector, a gas-detecting apparatus, a gas-detecting system, a method of manufacturing a gas detector, and a vehicle mounted with a gas detector.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

[Modes for Carrying out the Invention]

A. First Embodiment

Figure 1:
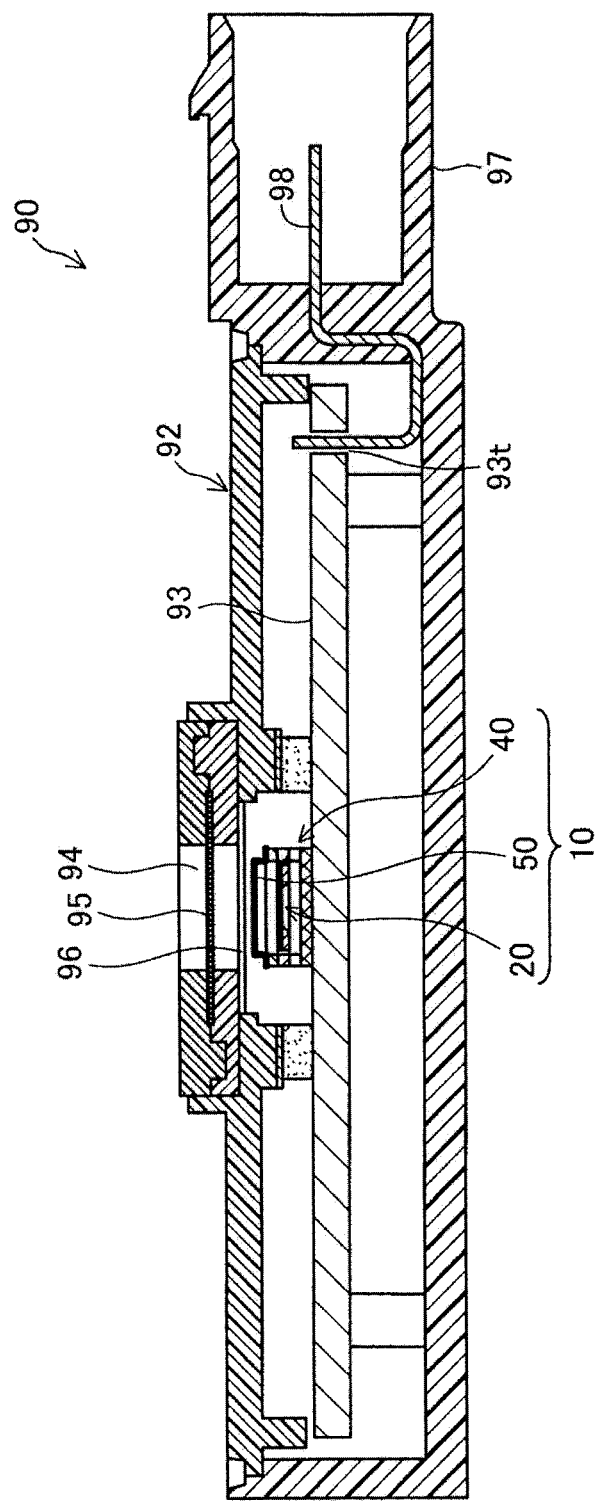
FIG. 1 is a sectional view showing a gas detector according to a first embodiment of the present invention.

FIG. 1 is a view for explaining a gas detector 90 according to a first embodiment of the present invention. The gas detector 90 includes a thermal conduction type detecting element assembly 10 which detects the concentration of gas to be detected through utilization of thermal conduction to the gas to be detected. The detecting element assembly 10 has a detecting element 20, a base 40 for the detecting element 20, and a protection cap 50. The configuration of the detecting element assembly 10 will be described later. In the gas detector 90, a housing 92 houses a wiring board 93 on which the detecting element assembly 10 is mounted. The housing 92 is formed of an electrically nonconductive resin. The housing 92 is also called the "housing case 92," and the wiring board 93 is also called the "circuit board 93." On the wiring board 93, there are mounted, by means of soldering, electronic components (including a temperature-measuring circuit and a gas-detecting circuit) for driving and controlling the detecting element 20. However, all of or a part of these electronic components may be mounted externally of the gas detector 90 of FIG. 1. The housing 92 of the gas detector 90 has a gas introduction section 94 for introducing gas to be detected into the housing 92. The gas introduction section 94 is also called the "gas introduction hole 94." In the gas introduction hole 94, there is provided a metal member 95 (also called the "metal mesh member 95") having a plurality of gas flow passages for allowing passage of gas to be detected. In the present embodiment, the metal member 95 is a metal mesh. The metal member 95 is provided for the purpose of preventing outward jetting of flame (flame arrester function) generated through ignition of flammable gas to be detected as a result of large increase in temperature of a heat-generating resistor (which will be described later) of the detecting element 20. In order to achieve the purpose, preferably, the metal member 95 covers the gas introduction hole 94 (i.e., the metal member 95 is provided over the entire range of the gas introduction hole 94). The metal member 95 assumes the form of a plate and is externally exposed, and the detecting element 20 is disposed under the main surface of the metal member 95 in the form of a plate. That is, the detecting element 20 is disposed under or immediately under the metal member 95.

The expression "the detecting element 20 is disposed under the metal member 95" means that, when the metal member 95 is projected in a downward direction, the detecting element 20 lies in a projected image of the metal member 95, where a direction perpendicular to the surface of the wiring substrate 93 is a vertical direction, and a direction directed toward the wiring substrate 93 from the metal member 95 is the downward direction. Therefore, the term "under" does not necessarily mean "vertically under." The reason for disposing the detecting element 20 under the metal member 95 is as follows: when gas to be detected is introduced from the gas introduction hole 94, the gas immediately reaches the detecting element 20, so that response in gas detection is enhanced. No particular limitation is imposed on the metal member 95, so long as the metal member 95 has a plurality of gas flow passages. For example, in addition to a metal mesh, a porous metal member can be employed as the metal member 95. A water repellent filter 96 is disposed under the metal member 95 in such a manner as to cover the gas introduction hole 94. The water repellent filter 96 prevents entry of water from the gas introduction hole 94. The housing 92 has a connector 97 extending outward from one end thereof. The connector 97 is used to establish electrical connection to an external circuit. A plurality of connector pins 98 are provided within the connector 97. The wiring board 93 has a plurality of through holes 93t formed therein for connection to the respective connector pins 98. The connector pins 98 are inserted through the respective through holes 93t and fixed to the wiring board 93 by soldering.

The gas detector 90 is disposed, for example, in a system (e.g., a fuel cell vehicle or a household fuel cell system) in which a fuel cell stack, which utilizes hydrogen gas as energy source, is installed, for detecting hydrogen gas, which is flammable gas. Thus, the gas detector 90 can detect leakage of hydrogen gas in the system.

Figure 2:
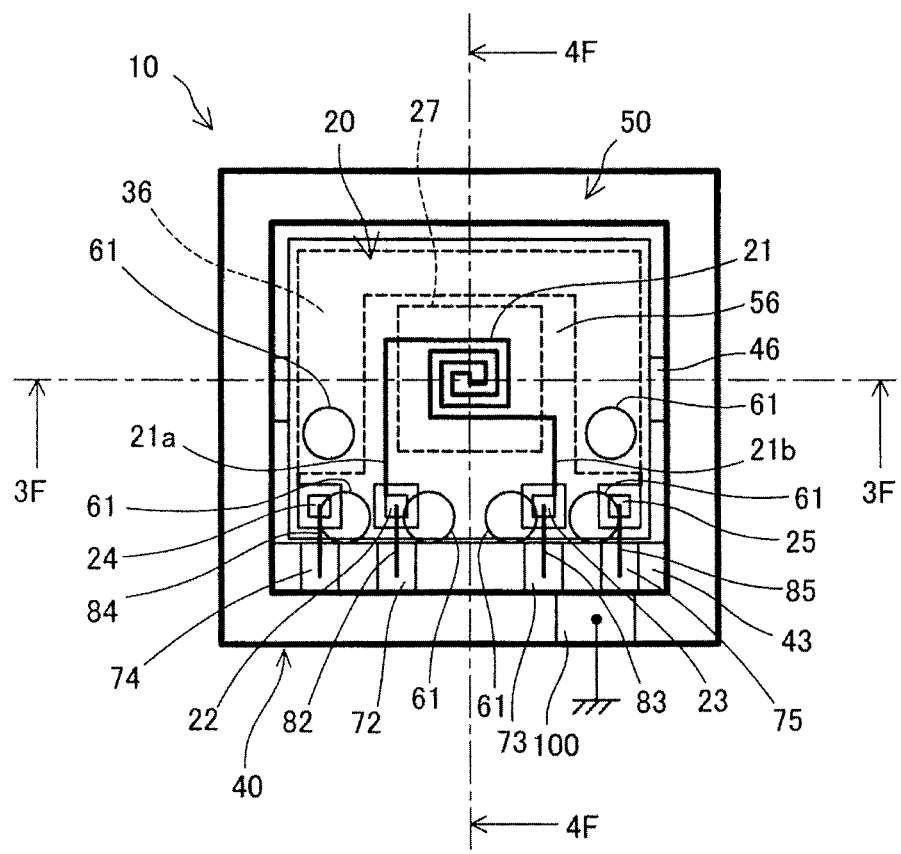
FIG. 2 is a top view showing a detecting element assembly in the first embodiment.
Figure 3:
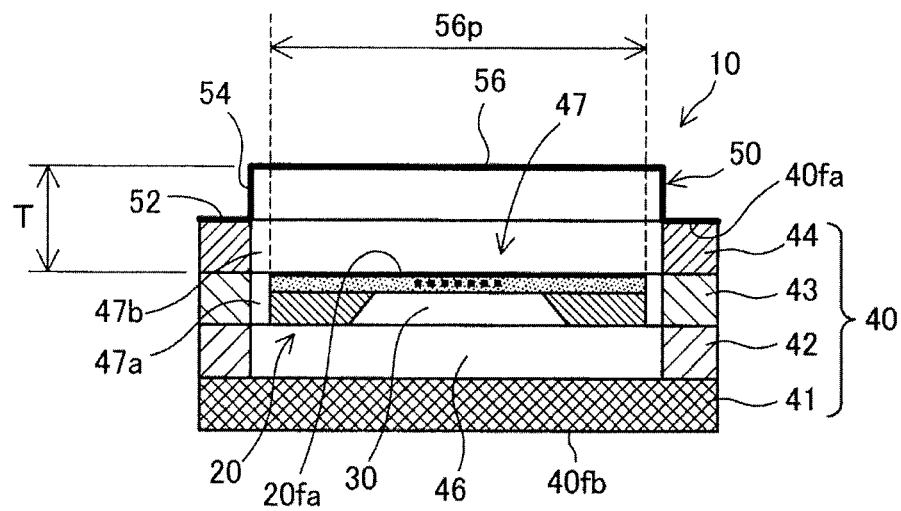
FIG. 3 is a sectional view taken along line 3F-3F of FIG. 2.
Figure 4:
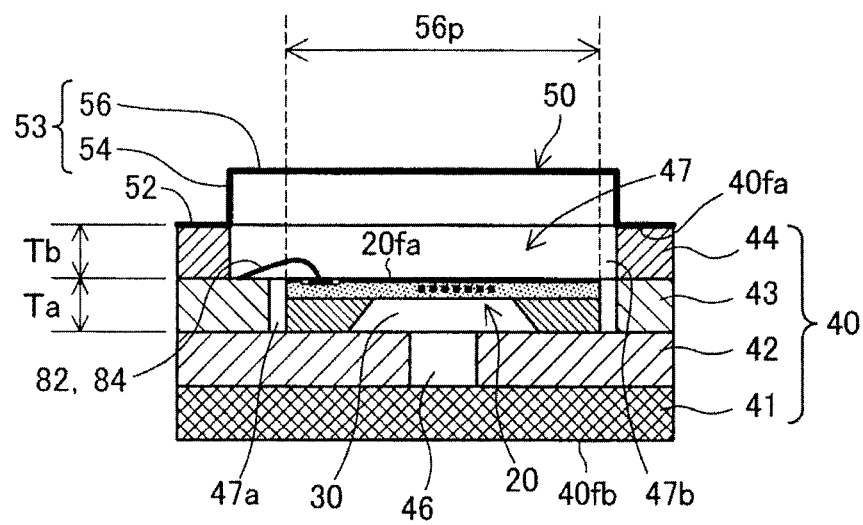
FIG. 4 is a sectional view taken along line 4F-4F of FIG. 2.
Figure 5:
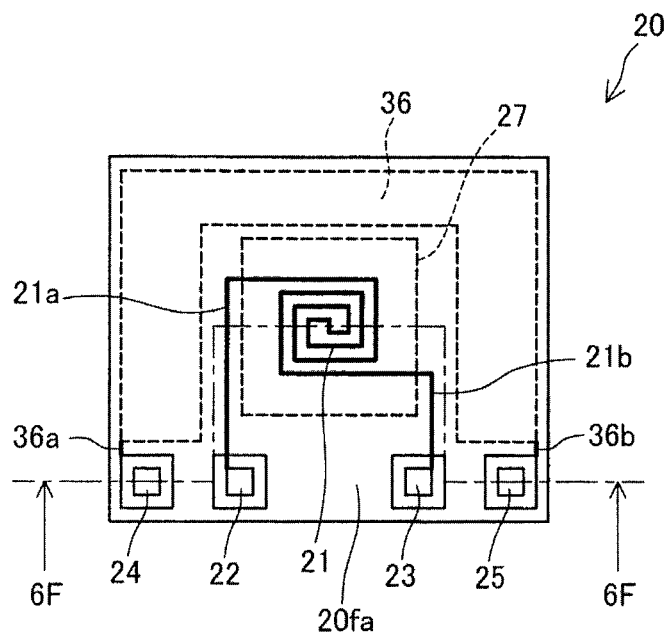
FIG. 5 is a top view showing a detecting element of the detecting element assembly.
Figure 6:
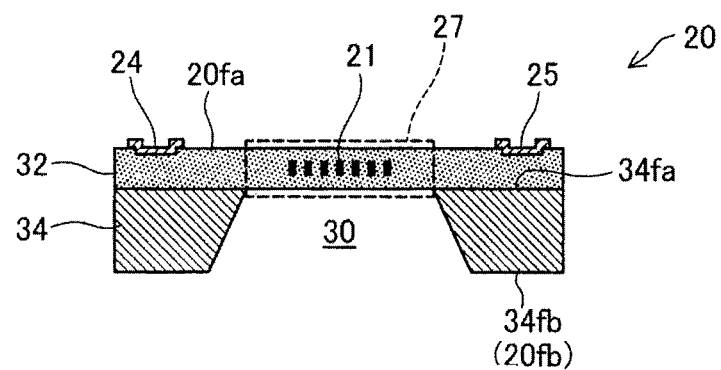
FIG. 6 is a sectional view taken along line 6F-6F of FIG. 5.

FIG. 2 is a top view showing the detecting element assembly 10 in the first embodiment. FIG. 3 is a sectional view taken along line 3F-3F of FIG. 2. FIG. 4 is a sectional view taken along line 4F-4F of FIG. 2. FIG. 5 is a top view showing the detecting element 20 of the detecting element assembly 10. FIG. 6 is a sectional view taken along line 6F-6F of FIG. 5. In order to facilitate understanding, FIG. 2 also shows members (e.g., a heat-generating resistor 21) hidden behind the protection cap 50. The upper side in FIGS. 3, 4, and 6 corresponds to the upper side of the detecting element assembly 10, and the lower side corresponds to the lower side of the detecting element assembly 10. With reference to FIGS. 2 to 6, the configuration of the detecting element assembly 10 will be described.

The detecting element assembly 10 shown in FIG. 2 is of a thermal conduction type and detects the concentration of gas to be detected through utilization of thermal conduction to the gas to be detected. The detecting element assembly 10 is disposed, for example, in a system (e.g., a fuel cell vehicle or a household fuel cell system) in which a fuel cell stack, which utilizes hydrogen gas as energy source, is installed, for detecting hydrogen gas, which is flammable gas. Thus, the detecting element assembly 10 can detect leakage of hydrogen gas in the system.

As shown in FIGS. 3 and 4, the detecting element assembly 10 includes the detecting element 20, the element base 40 on which the detecting element 20 is disposed, and the protection cap 50 attached to the element base 40 in such a manner as to cover the detecting element 20. As will be described later in detail, the protection cap 50 is connected to a grounding line of the circuit board 93 (FIG. 1) and functions as a detecting element wiring fusing prevention member for preventing or restraining a fusing (breakage) of internal wiring of the detecting element 20 which could otherwise be caused by static electricity. The designation "detecting element wiring fusing prevention member" may be replaced with "detecting element wiring fusing restraint member," "detecting element wiring breakage prevention member," or "detecting element wiring breakage restraint member."

As shown in FIGS. 5 and 6, as viewed from a top surface 20fa, the detecting element 20 has a substantially rectangular outline. The detecting element 20 includes a substrate 34 formed of silicon (Si), an insulating layer 32 disposed on the substrate 34, the heat-generating resistor 21 embedded in the insulating layer 32, a temperature-measuring resistor 36 embedded in the insulating layer 32, and first to fourth electrodes 22 to 25.

As shown in FIG. 6, the substrate 34 assumes the form of a plate and has a first surface 34fa on which the insulating layer 32 is disposed, and a second surface 34fb opposite the first surface 34fa. The second surface 34fb forms a back surface (lower surface) 20fb of the detecting element 20 opposite the top surface 20fa. In a view of the detecting element 20 as viewed from the top surface 20fa, the substrate 34 has a cavity 30 (opening portion 30) in the form of a through hole extending therethrough from the first surface 34fa to the second surface 34fb.

The insulating layer 32 is formed of an electrically insulating material, such as silicon dioxide ($SiO_2$) or silicon nitride ($Si_3N_4$). Also, the insulating layer 32 may be formed of a single material or may has a laminate structure in which layers of different materials are laminated.

The heat-generating resistor 21 varies in resistance with temperature thereof which varies with the temperature of (more specifically, thermal conduction to) gas to be detected. The heat-generating resistor 21 is formed of an electrically conductive material having high temperature coefficient of resistance. In the first embodiment, the heat-generating resistance 21 is formed of platinum (Pt). As shown in FIG. 5, the heat-generating resistor 21 has a spiral form.

In the case of detection of hydrogen gas, which is flammable gas, the amount of heat removed from the heat-generating resistor 21 as a result of thermal conduction to hydrogen gas corresponds to hydrogen gas concentration. Thus, on the basis of a change in resistance of the heat-generating resistor 21, hydrogen gas concentration can be detected.

The heat-generating resistor 21 is disposed in a thin film section 27 in contact with the cavity 30 of the insulating layer 32. That is, the cavity 30 is located immediately under the heat-generating resistor 21. In this manner, through disposition of the heat-generating resistor 21 in the thin film section 27, the heat-generating resistor 21 is thermally insulated from the surrounding environment. That is, there can be reduced the amount of heat conducted from the heat-generating resistor 21 to the substrate 34. Thus, the heat-generating resistor 21 can be increased or decreased in temperature in a short period of time, whereby power consumption of the heat-generating resistor 21 can be reduced. The thin film section 27 is exposed to an analyte atmosphere (fluid containing gas to be detected).

As shown in FIG. 5, one end (left end in the drawing) of the heat-generating resistor 21 is connected to a wiring line 21a disposed in the insulating layer 32 and formed integral with the heat-generating resistor 21. The other end (right end in the drawing) of the heat-generating resistor 21 is connected to a wiring line 21b disposed in the insulating layer 32 and formed integral with the heat-generating resistor 21.

The temperature-measuring resistor 36 detects the temperature of fluid (atmospheric gas) residing on the detecting element 20 and containing gas to be detected. As shown in FIG. 5, the temperature-measuring resistor 36 is disposed externally of the heat-generating resistor 21 in such a manner as to partially surround the perimeter of the heat-generating resistor 21. Similar to the heat-generating resistor 21, the temperature-measuring resistor 36 is formed within the insulating layer 32. The temperature-measuring resistor 36 is formed of an electrically conductive material whose resistance varies in proportion to temperature. In the first embodiment, the temperature-measuring resistor 36 is formed of platinum. The temperature-measuring resistor 36 in the first embodiment increases in resistance with temperature. The temperature-measuring resistor 36 is configured such that a thin platinum pattern is formed in a region indicated by reference numeral 36, but the illustration of the pattern is omitted.

As shown in FIG. 5, the first to fourth electrodes 22 to 25 are disposed on the top surface 20fa along one side of the top surface 20fa. The first to fourth electrodes 22 to 25 are formed of, for example, aluminum (Al) or gold (Au). The first electrode 22 is electrically connected to the heat-generating resistor 21 through the wiring line 21a. The second electrode 23 is electrically connected to the heat-generating resistor 21 through the wiring line 21b. The third electrode 24 is electrically connected to the temperature-measuring resistor 36 through a wiring line 36a. The fourth electrode 25 is electrically connected to the temperature-measuring resistor 36 through a wiring line 36b. The first electrode 22, the second electrode 23, and the heat-generating resistor 21 partially constitute a gas-detecting circuit provided on a printed wiring board, which will be described later. Specifically, the gas-detecting circuit includes the Wheatstone bridge composed of the heat-generating resistor 21 and three fixed resistances. The gas-detecting circuit controls the heat-generating resistor 21 such that the heat-generating resistor 21 has a fixed temperature. The first electrode 22 outputs a voltage indicative of the concentration of gas to be detected, and the second electrode 23 and the fourth electrode 25 are grounded. The third electrode 24, the fourth electrode 25, and the temperature-measuring resistor 36 partially constitute a temperature-measuring circuit provided on the printed wiring board. Specifically, the temperature-measuring circuit includes the Wheatstone bridge composed of the temperature-measuring resistor 36 and three fixed resistances. The third electrode 24 outputs a voltage indicative of the temperature of atmospheric gas, and the fourth electrode 25 is grounded.

As shown in FIGS. 3 and 4, the electrically insulative element base 40 has the form of a substantially rectangular parallelepiped. The element base 40 has a recess 47 for accommodating the detecting element 20 therein. The element base 40 is a multilayer substrate in which first to fourth ceramic insulating layers 41 to 44 formed of alumina are laminated in this order. The first to fourth ceramic insulating layers 41 to 44 each have a substantially rectangular parallelepiped shape.

The detecting element 20 is disposed on the second ceramic insulating layer 42. Specifically, the detecting element 20 is fixed on the second ceramic insulating layer 42 with an adhesive such as epoxy resin.

As shown in FIGS. 3 and 4, the second ceramic insulating layer 42 has a communication groove 46 formed therein for allowing communication between the cavity 30 of the substrate 34 and an ambient atmosphere around the detecting element assembly 10. More specifically, the cavity 30 and the ambient atmosphere communicate with each other through a gap between the element base 40 and the detecting element 20. The communication groove 46 extends straight and is formed immediately under the cavity 30. By virtue of the element base 40 having the communication groove 46, sealing the cavity 30 can be prevented. This can reduce the possibility of the cavity 30 being filled with adhesive, which could otherwise result from an increase in the amount of application of the adhesive. Also, since pressure variations of the cavity 30 can be restrained, the possibility of breakage of the thin film section 27 can be reduced.

The third ceramic insulating layer 43 is disposed on the second ceramic insulating layer 42. The third ceramic insulating layer 43 has a first through hole 47a formed therein which has a substantially rectangular parallelepiped shape and partially constitutes the recess 47. The detecting element 20 has the same thickness as that of the third ceramic insulating layer 43 and is disposed within the first through hole 47a.

First to fourth electrode pads 72 to 75 (FIG. 2) corresponding to the first to fourth electrodes 22 to 25 of the detecting element 20 are disposed on the third ceramic insulating layer 43. The first to fourth electrode pads 72 to 75 are formed of, for example, Al or Au. The first to fourth electrodes 22 to 25 and the corresponding first to fourth electrode pads 72 to 75 are electrically connected to each other through first to fourth bonding wires 82 to 85, respectively. Unillustrated internal wiring lines connected to the corresponding first to fourth electrode pads 72 to 75 run up to a back surface 40fb (FIG. 3) of the element base 40. Thus, the first to fourth electrode pads 72 to 75 are electrically connected, by soldering or the like, to the printed wiring board which has a circuit for detecting the concentration of gas to be detected.

As shown in FIGS. 3 and 4, the fourth ceramic insulating layer 44 has a second through hole 47b formed therein which has a substantially rectangular parallelepiped shape and partially constitutes the recess 47. The upper surface of the fourth ceramic insulating layer 44 forms a top surface 40fa of the element base 40. Referring to FIG. 4, preferably, a distance Tb (element-to-base distance Tb) between the top surface 20fa and the top surface 40fa of the element base 40 along a direction perpendicular to the top surface 20fa (vertical direction in FIG. 4) is less than three times a length (dimension) Ta of the detecting element 20 along the direction perpendicular to the top surface 20fa (i.e., a thickness Ta of the detecting element 20). By virtue of this dimensional relation, the element base 40 can be reduced in dimension with respect to the direction perpendicular to the top surface 20fa of the detecting element 20. In the detecting element assembly 10 in the first embodiment, Tb and Ta assume a same value of about 0.4 mm.

As shown in FIGS. 3 and 4, the protection cap 50 is attached to the top surface 40fa of the element base 40 with an adhesive such as epoxy resin. The protection cap 50 is formed of metal. Preferably, a metal (e.g., Kovar or 42Alloy) whose linear expansion coefficient is close to that of the element base 40 is used to form the protection cap 50. Employment of such a metal can reduce the possibility of breakage of bond, which could otherwise result from a difference in linear expansion coefficient between the two members 40 and 50.

The protection cap 50 protrudes upward. The protection cap 50 includes a brim-like attachment portion 52 and a protruding portion 53 protruding upward (in a direction away from the top surface 40fa) from the attachment portion 52. The protruding portion 53 includes a standing portion 54 extending vertically upward from the attachment portion 52, and a rectangular-plate-like top surface portion 56 connected to the standing portion 54 and being in parallel with the top surface 20fa. The attachment portion 52 has a shape corresponding to the top surface 40fa. The attachment portion 52 is attached to the top surface 40fa. Also, the attachment portion 52 is in surface contact with the top surface 40fa. "Surface contact" encompasses direct contact and contact through adhesive or the like. The standing portion 54 is adapted to adjust the distance (along a direction perpendicular to the top surface 20fa) between the top surface 20fa and the top surface portion 56 (more specifically, that back surface of the top surface portion 56 which faces the top surface 20fa). The top surface portion 56 is disposed above the top surface 20fa. The direction perpendicular to the top surface 20fa corresponds to the vertical direction in FIGS. 3 and 4.

The protection cap 50 has six gas passage holes 61 (FIG. 2) formed in the top surface portion 56 for introducing atmospheric gas containing gas to be detected, into the interior thereof. For convenience of illustration, FIG. 2 shows a view seeing through the top surface portion 56 of the protection cap 50. The gas passage holes 61 are not disposed immediately above the thin film section 27 (a central section of the insulating layer 32 where the heat-generating resistor 21 is embedded). That is, in a view of the detecting element assembly 10 as viewed from the top surface 20fa side, the gas passage holes 61 do not overlie the thin film section 27. By virtue of such disposition of the gas passage holes 61, even when foreign matter (e.g., dust and pipe chips) contained in atmospheric gas enters the interior of the protection cap 50 through the gas passage holes 61, there can be reduced the possibility that entering foreign matter hits the thin film section 27. Thus, there can be reduced the possibility of breakage of the heat-generating resistor 21 formed in the thin film section 27. Also, there can be restrained conduction of heat generated by the heat-generating resistor 21 to foreign matter adhering to the thin film section 27. Thus, there can be further improved accuracy in detecting the concentration of gas to be detected, by use of the detecting element assembly 10.

Preferably, a separation distance T is 0.5 mm or more, where, as shown in FIG. 3, the separation distance T is the shortest distance in a direction perpendicular to the top surface 20fa of the detecting element 20 between the top surface 20fa and an immediately above portion 56p (more specifically, that surface of the immediately above portion 56p which faces the top surface 20fa) of the protection cap 50 located immediately above the detecting element 20. Through employment of such a separation distance T, there can be reduced the amount of heat transferred from the heat-generating resistor 21 to the protection cap 50. Thus, there can be improved accuracy in detecting the concentration of gas to be detected, by use of the detecting element assembly 10.

The wiring board 93 (FIG. 1) of the gas detector 90 includes a circuit for detecting the concentration of gas to be detected (a gas-detecting circuit and a temperature-measuring circuit). The concentration of gas to be detected is detected by use of a publicly known technique (refer to, for example, Japanese Patent No. 5102172). Specifically, the concentration of gas-to-be-detected introduced into the protection cap 50 is detected on the basis of the relation between temperature information output from the temperature-measuring circuit which includes the temperature-measuring resistor 36 and other resistances, and concentration information (voltage between the electrodes 22 and 23 of the heat-generating resistor 21) output from the gas-detecting circuit which includes the heat-generating resistor 21 and other resistances.

For example, in the case of detection of the concentration of hydrogen gas to be detected, the amount of heat removed from the heat-generating resistor 21 as a result of thermal conduction to hydrogen gas corresponds to hydrogen gas concentration. Thus, on the basis of a change in terminal-to-terminal voltage of the heat-generating resistor 21 controlled at a fixed temperature, hydrogen gas concentration can be detected. Since the terminal-to-terminal voltage of the heat-generating resistor is influenced by the temperature of gas to be detected, by use of temperature detected on the basis of resistance of the temperature-measuring resistor 36, hydrogen gas concentration detected on the basis of terminal-to-terminal voltage of the heat-generating resistor 21 is corrected.

As shown in FIG. 2, a grounding electrode pad 100 is provided on the top surface of the element base 40 for grounding the protection cap 50. In the first embodiment, by means of grounding the protection cap 50 which functions as a detecting element wiring fusing prevention member, there is reduced the possibility that static electricity causes breakage of internal wiring of the detecting element 20.

The grounding electrode pad 100 is electrically connected to a second electrode pad 73 provided on the third ceramic insulating layer 43. As mentioned above, the second electrode pad 73 is connected to the second electrode 23 of the detecting element 20, and the second electrode 23 is grounded. Specifically, the second electrode 23 is connected to a grounding line provided on the surface of the wiring board 93 (FIG. 1) through an electrode pad provided on the bottom surface of the element base 40. Because of such a state of connection, in FIG. 2, the grounding electrode pad 100 is illustrated as being grounded.

Figure 7:
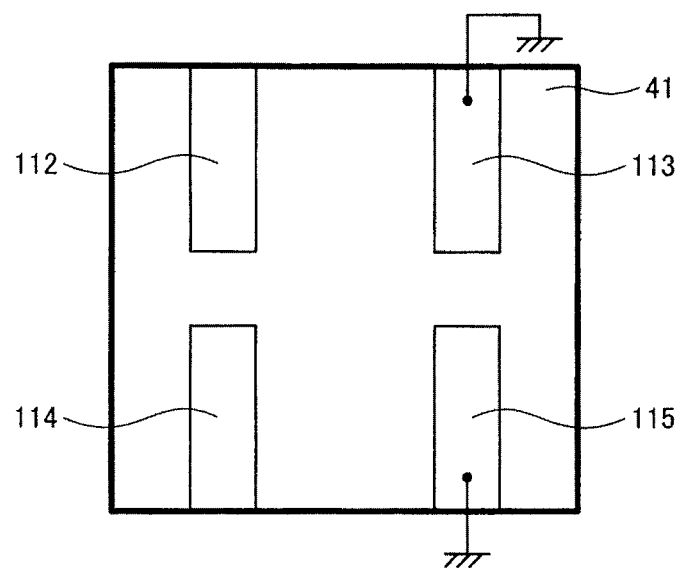
FIG. 7 is a bottom view of an element base of the detecting element assembly.

FIG. 7 shows the bottom surface of the element base 40; i.e., the bottom surface of the first ceramic insulating layer 41. Four electrode pads 112 to 115 are formed on the bottom surface of the first ceramic insulating layer 41. These electrode pads 112 to 115 are connected to the electrodes 22 to 25, respectively, of the detecting element 20 and to wiring patterns provided on the surface of the wiring board 93 (FIG. 1). The second electrode pad 113 and the fourth electrode pad 115 are connected to a grounding line on the wiring board 93. In this manner, in the first embodiment, the metal protection cap 50 of the detecting element 20 is electrically connected to the grounding line on the wiring board 93 through the grounding electrode members 100, 73, 23, and 113.

In order to examine whether or not the electrostatic breakage of wire occurs in the detecting element 20, the following electrostatic discharge immunity test was conducted on the gas detector of the first embodiment.
<Electrostatic Discharge Immunity Test>
(1) Test Standard
The electrostatic discharge immunity test was conducted in accordance with ISO 10605 Ed2.0:2008.
(2) Test Conditions
Output voltage: ±25 Kv (air discharge)
Current rise time: 0.7 ns to 1.0 ns
Storage capacitance: 330 pF
Discharge resistance: 2 kΩ
Test count: 3 times with positive and negative polarities
Test cycle: one second Ambient temperature: 25±10° C., ambient humidity: 20% RH to 60% RH
Power supply to gas detector: supplied
Electrostatic discharge point: in the vicinity of metal member (FIG. 12) in gas introduction hole 94
(3) Criterion
After electrostatic discharge, judgment is formed on the basis of whether or not the gas detector malfunctions.
(4) Test Results
The gas detector (a system in which the protection cap 50 is grounded) of the first embodiment was free from any abnormality. By contrast, a gas detector of a comparative example in which the protection cap 50 was not grounded suffered from breakage of internal wiring of the detection element 20.

The test has experimentally revealed that grounding the protection cap 50 can reduce the possibility that static electricity causes breakage of internal wiring of the detecting element 20, as compared with the case where the protection cap 50 is not grounded. The gas detector of the first embodiment and the gas detector of the comparative example subjected to the electrostatic discharge immunity test are configured such that, as described with reference to FIG. 1, the metal member 95 is provided in such a manner as to cover the gas introduction hole 94, and the detecting element 20 is disposed under the metal member 95. Such a configuration involves the following problem: static electricity discharged in the vicinity of the gas introduction hole 94 is apt to reach the metal member 95 and, furthermore, tends to reach the detecting element 20 from the metal member 95. Desirably, even when static electricity is discharged to the gas detector, the gas detector is free from malfunction and accurately detects gas concentration. However, as mentioned above, in the case where the gas detector 90 is configured such that the detecting element 20 is disposed under the gas introduction hole 94, there has been the possibility that static electricity discharged in the vicinity of the gas introduction hole 94 reaches the detecting element 20 and causes breakage of internal wiring (e.g., the resistor 21 or 36) of the detecting element 20, resulting in malfunction of the gas detector 90. Even under such a condition, the gas detector of the first embodiment can reduce the possibility that static electricity causes breakage of internal wiring of the detecting element 20. Such an advantage derives from a configurational feature that the shortest distance between the metal member 95 and the protection cap 50 is smaller than that between the metal member 95 and the detecting element 20. Specifically, even when static electricity is discharged to the metal member 95, static electricity flows to the wiring board 93 through the protection cap 50 which is closer to the metal member 95, so that static electricity does not flow in a large amount to the detecting element 20. Thus, there can be prevented or restrained fusing (breakage) of internal wiring of the detecting element 20 which could otherwise be caused static electricity. As understood from the above description, the metal protection cap 50 functions as a detecting element wiring fusing prevention member for preventing or restraining fusing (breakage) of internal wiring of the detecting element 20 which could otherwise be caused by static electricity.

In the case where the protection cap 50 is fixed on the element base 40 with an adhesive, using an electrically conductive adhesive is preferred for securing an electrical connection between the protection cap 50 and the grounding electrode pad 100. In the case of use of an electrically nonconductive adhesive, preferably, the adhesive is not applied onto the grounding electrode pad 100, and the adhesive is applied only to that portion of the top surface of the element base 40 where the grounding electrode pad 100 does not exist. In this case, some contact resistance may arise between the protection cap 50 and the grounding electrode pad 100. However, even in this case, if the electrical resistance between the protection cap 50 and a grounding line on the wiring board 93 is equal to or smaller than $\frac{1}{10}$ the resistance of the heat-generating resistor 21 or the resistance of the temperature-measuring resistor 36, whichever smaller, there can be sufficiently reduced the above-mentioned possibility of breakage of internal wiring of the detecting element 20 caused by static electricity. Herein, the expression "the protection cap 50 is grounded" or "the protection cap 50 is electrically connected to a grounding line" means that the electrical resistance between the protection cap 50 and the grounding line of the wiring board 93 is as low as a grounded state. If such a state of connection can be implemented, an electrically nonconductive adhesive may be applied to the entire top surface of the element base 40 including the grounding electrode pad 100. However, preferably, the state of connection is such that the protection cap 50 and the grounding line of the wiring board 93 are considered to be short-circuited (the state in which the electrical resistance between them is less than 10Ω).

B. Second Embodiment

Figure 8:
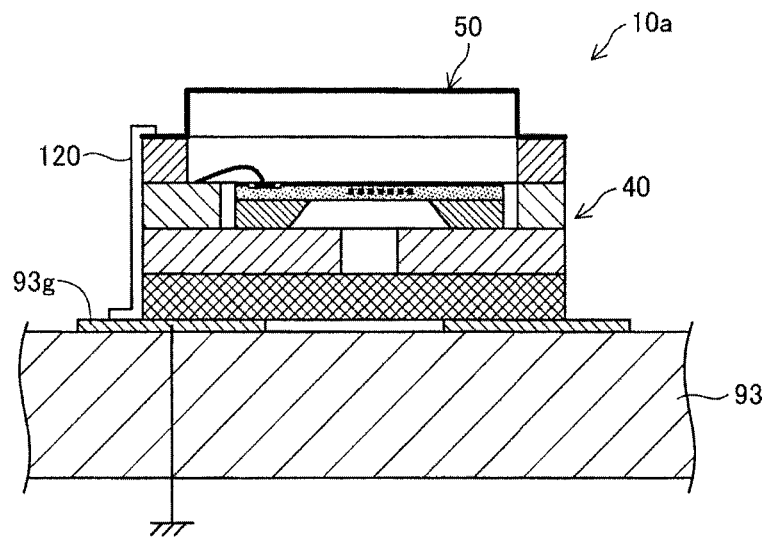
FIG. 8 is a view showing a portion of a gas detector according to a second embodiment of the present invention.

FIG. 8 is an explanatory view showing a portion of a gas detector according to a second embodiment of the present invention. FIG. 8 shows a state in which a detecting element assembly 10a is fixed on the wiring board 93 of the gas detector 90 (FIG. 1). The detecting element assembly 10a differs from the detecting element assembly 10 of the first embodiment only in that the grounding electrode pad 100 (FIG. 2) for grounding the protection cap 50 is not provided. Other configurational features of the second embodiment are similar to those of the first embodiment. Although unillustrated, other portions of the gas detector are similar to those shown in FIG. 1.

The second embodiment is characterized in that the metal protection cap 50 is electrically connected to a grounding line 93g on the wiring board 93 by means of an electrically conductive paste 120 applied to the side surface of the element base 40. This configuration also allows the protection cap 50 to be grounded; as a result, there can be reduced the possibility of breakage of internal wiring of the detecting element 20 caused by static electricity. As can also be understood from this example, preferably, the protection cap 50 is grounded through a certain path. However, the configuration of the first embodiment shown in FIG. 2 is preferred, since the grounding electrode pad 100 is merely provided on the element base 40 without need to employ an additional grounding member(s); i.e., the protection cap 50 can be grounded with minimal member and space.

In the above-described first and second embodiments, since the protection cap 50 functioning as a detecting element wiring fusing prevention member is fixed on the element base 40, the detecting element wiring fusing prevention member can be positioned more easily than in the case where the detecting element wiring fusing prevention member is directly provided on a circuit board.

C. Third Embodiment

Figure 9:
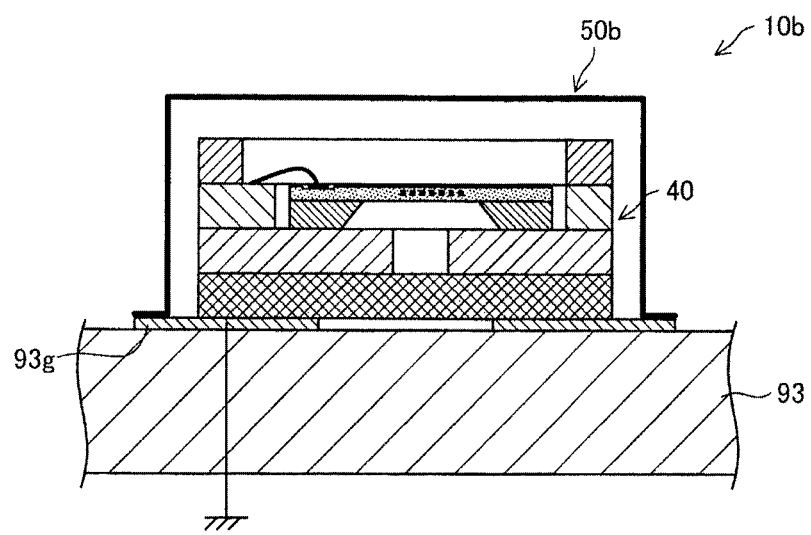
FIG. 9 is a view showing a portion of a gas detector according to a third embodiment of the present invention.

FIG. 9 is an explanatory view showing a portion of a gas detector according to a third embodiment of the present invention. A detecting element assembly 10b of the third embodiment differs from the detecting element assembly 10a of the second embodiment (FIG. 8) only in that the protection cap 50 thereof is not fixed on the top surface of the element base 40, but is fixed on the wiring board 93 of the gas detector 90 (FIG. 1). Other configurational features of the third embodiment are similar to those of the second embodiment. In the third embodiment, similar to the case of the second embodiment, the grounding electrode pad 100 (FIG. 2) for grounding the protection cap 50 is not provided.

In the third embodiment, a metal protection cap 50b has such a substantially rectangular parallelepiped shape as to cover the element base 40. A space is provided between the protection cap 50b and the element base 40. The protection cap 50b is soldered to a grounding line 93g on the wiring board 93 at a peripheral position around the element base 40. This configuration also allows the protection cap 50b functioning as a detecting element wiring fusing prevention member to be grounded; as a result, there can be reduced the possibility of breakage of internal wiring of the detecting element 20 caused by static electricity.

In the above-described first to third embodiments, since the protection cap 50 (50b) functioning as a detecting element wiring fusing prevention member covers the detection element 20 from above, the protection cap 50 (50b) can not only protect the detecting element 20 from static electricity but also physically protect the detecting element 20.

D. Fourth Embodiment

Figure 10:
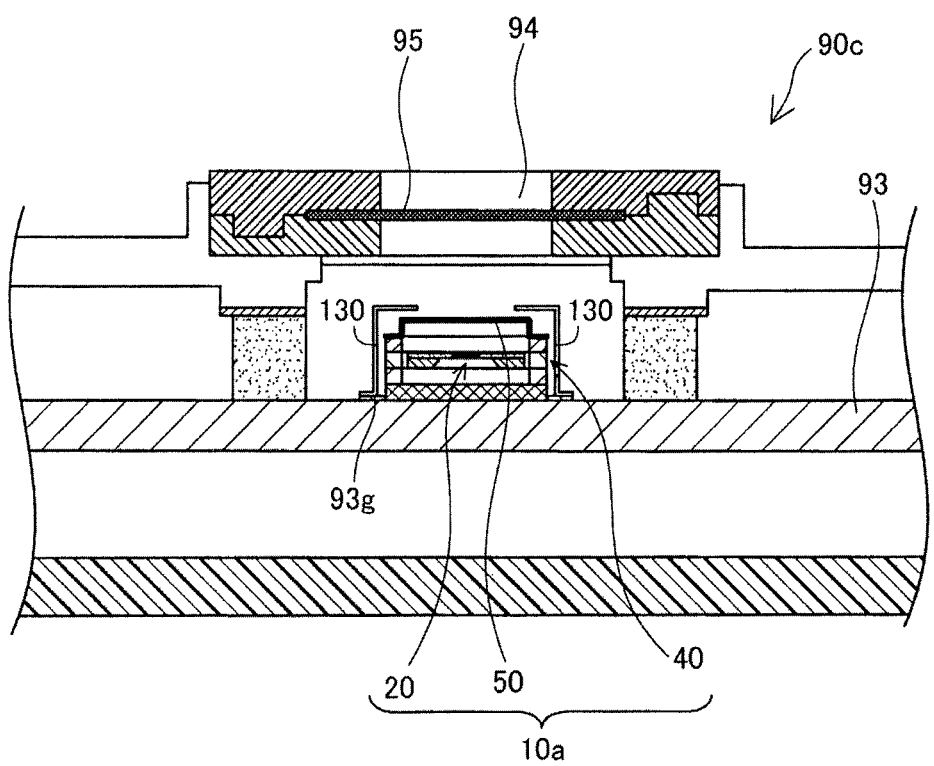
FIG. 10 is a view showing a portion of a gas detector according to a fourth embodiment of the present invention.

FIG. 10 is an explanatory view showing a portion of a gas detector according to a fourth embodiment of the present invention. In the fourth embodiment, separately from the protection cap 50, an electrically conductive grounding member 130 functioning as a detecting element wiring fusing prevention member is provided around the detecting element assembly 10a (FIG. 8) of the second embodiment. The grounding member 130 has a substantially rectangular parallelepiped shape whose top surface located above the detecting element 20 has a rectangular opening. Also, the grounding member 130 is soldered to the grounding line 93g on the wiring board 93. The grounding member 130 is disposed at a position such that the shortest distance between the metal member 95 and the grounding member 130 is smaller than the shortest distance between the metal member 95 and the detecting element 20. Therefore, by a principle similar to that in the case of the first to third embodiments, the grounding member 130 functioning as a detecting element wiring fusing prevention member can reduce the possibility of breakage of internal wiring of the detecting element 20 caused by static electricity.

As can be understood from the first to fourth embodiments, the detecting element wiring fusing prevention member can be implemented by use of an electrically conductive member in any shape, so long as the detecting element wiring fusing prevention member is disposed at a position such that the shortest distance between the metal member 95 and the detecting element wiring fusing prevention member is smaller than the shortest distance between the metal member 95 and the detecting element 20. For example, an electrically conductive rod member or mesh member can be utilized as the detecting element wiring fusing prevention member.

E. Modified Embodiments

Modified Embodiment 1

In the first embodiment, the protection cap 50 has the gas passage hole 61 formed therein for introducing therein atmospheric gas which contains gas to be detected. However, the gas passage is not limited to the gas passage hole 61, so long as the gas passage allows introduction of atmospheric gas into the protection cap 50. For example, portions of the protection cap 50 may be cut out to form apertures or slits for use as the gas passage, or a portion of the protection cap 50 may be formed of metal mesh for use as the gas passage. The position of such a gas passage of the protection cap 50 is not limited to the top surface of the protection cap 50, but the gas passage may be provided at the side surface of the protection cap 50.

Modified Embodiment 2

In the embodiments described above, the element base 40 is formed of ceramic. However, the present invention is not limited thereto, so long as the element base 40 is formed of an electrically insulative material. For example, the element base 40 may be formed of a heat-resistant resin.

The present invention is not limited to the above-described embodiments and modified embodiments, but may be embodied in various other forms without departing from the spirit of the invention. For example, in order to solve, partially or entirely, the above-mentioned problem or yield, partially or entirely, the above-mentioned effects, technical features of the embodiments and modified embodiments corresponding to technical features of the modes described in the section "Summary of the Invention" can be replaced or combined as appropriate. Also, the technical feature(s) may be eliminated as appropriate unless the present specification mentions that the technical feature(s) is mandatory.

DESCRIPTION OF REFERENCE NUMERALS 10, 10a, 10b: detecting element assembly
20: detecting element
20fa: top surface
20fb: back surface
21: heat-generating resistor
21a: wiring line
21b: wiring line
22: first electrode
23: second electrode
24: third electrode
25: fourth electrode
27: thin film section
30: cavity (opening portion)
32: insulating layer
34: substrate
34fa: first surface
34fb: second surface
36: temperature-measuring resistor
36a: wiring line
36b: wiring line
40, 40d: element base
40fa: top surface
40fb: back surface
40sa: side surface
41: first ceramic insulating layer
42: second ceramic insulating layer
43: third ceramic insulating layer
44: fourth ceramic insulating layer
46: communication groove
47: recess
47a: first through hole
47b: second through hole
50: protection cap (detecting element wiring fusing prevention member)
52: attachment portion
53: protruding portion
54: standing portion
56: top surface portion
56p: immediately above portion
61: gas passage hole
72: first electrode pad
73: second electrode pad
74: third electrode pad
75: fourth electrode pad
82: first bonding wire
83: second bonding wire
84: third bonding wire
85: fourth bonding wire
90: gas detector
92: housing (housing case)
93: wiring board (circuit board)
93t: through hole
94: gas introduction section (gas introduction hole)
95: metal member (metal mesh member)
96: water repellent filter
97: connector
98: connector pin
100: grounding electrode pad
112 to 115: electrode pad
130: grounding member (detecting element wiring fusing prevention member)

The invention claimed is:

1. A gas detector comprising: a detecting element that detects flammable gas; a circuit board electrically connected to the detecting element; a housing case having a gas introduction hole, and housing the detecting element and the circuit board; and a metal member disposed in the gas introduction hole and having a plurality of gas flow passages; and a detecting element wiring fusing prevention member, has gas passages there through, and is electrically conductive and electrically connected to a grounding line of the circuit board, wherein the detecting element is disposed under the metal member, and the detecting element wiring fusing prevention member is disposed at a position such that shortest distance between the metal member and the detecting element wiring fusing prevention member is smaller than a shortest distance between the metal member and the detecting element.

2. The gas detector according to claim 1, wherein the gas passage of the detecting element wiring fusing prevention member allows for the flammable gas to pass and is disposed in such a manner as to cover the detecting element.

3. The gas detector according to claim 1, wherein
the detecting element is disposed on a base fixed on the circuit board, and
the detecting element wiring fusing prevention member is fixed to the base.

4. The gas detector according to claim 3, wherein
the base is electrically insulative and has a grounding electrode pad formed thereon and electrically connected to the grounding line of the circuit board, and
the detecting element wiring fusing prevention member is electrically connected to the grounding electrode pad.

5. The gas detector according to claim 1, wherein
the metal member assumes a form of a plate and is externally exposed, and
the detecting element is disposed under a main surface of the metal member in the form of a plate.

6. The gas detector according to claim 2, wherein
the detecting element is disposed on a base fixed on the circuit board, and
the detecting element wiring fusing prevention member is fixed to the base.

7. The gas detector according to claim 2, wherein
the metal member assumes a form of a plate and is externally exposed, and
the detecting element is disposed under a main surface of the metal member in the form of a plate.

8. The gas detector according to claim 3, wherein
the metal member assumes a form of a plate and is externally exposed, and
the detecting element is disposed under a main surface of the metal member in the form of a plate.

9. The gas detector according to claim 4, wherein
the metal member assumes a form of a plate and is externally exposed, and
the detecting element is disposed under a main surface of the metal member in the form of a plate.

10. The gas detector according to claim 6, wherein
the metal member assumes a form of a plate and is externally exposed, and
the detecting element is disposed under a main surface of the metal member in the form of a plate.

11. The gas detector according to claim 1, wherein
the detecting element has a heat-generating resistor and a thin film section deposited on a top surface thereof, and
the heat-generating resistor is deposited in the thin film section and is thermally insulated from a surrounding environment.

12. The gas detector according to claim 11, wherein the gas passage of the detecting element wiring fusing prevention member allows for the flammable gas to pass, and no thin film section is deposited directly below the gas passage of the detecting element wiring fusing prevention member.

* * * * *